(12) United States Patent
Hasegawa et al.

(10) Patent No.: US 7,063,665 B2
(45) Date of Patent: Jun. 20, 2006

(54) HEALTH CARE SYSTEM

(75) Inventors: Hiroki Hasegawa, Tokyo (JP);
Kazuhiro Kosaka, Tokyo (JP);
Takahiko Nagatsuka, Tokyo (JP);
Michiko Uchikoshi, Saitama (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 10/785,028

(22) Filed: Feb. 25, 2004

(65) Prior Publication Data

US 2004/0199057 A1    Oct. 7, 2004

(30) Foreign Application Priority Data

Mar. 4, 2003    (JP)    ............... 2003-057010

(51) Int. Cl.
*A61B 5/00*    (2006.01)

(52) U.S. Cl. ............ 600/300; 128/920; 702/160

(58) Field of Classification Search ............ 702/19, 702/97, 160; 482/5–9, 900; 600/300–301, 600/481, 500, 503, 597; 128/903, 904, 920–925; 340/573.1; 705/2–4
See application file for complete search history.

(56) References Cited

U.S. PATENT DOCUMENTS 5,117,444 A * 5/1992 Sutton et al. ............. 702/97
6,327,495 B1 12/2001 Iwabuchi et al.
6,478,736 B1 * 11/2002 Mault ...................... 600/300
6,736,759 B1 * 5/2004 Stubbs et al. ............. 482/8

FOREIGN PATENT DOCUMENTS

JP    2000-229072 A    8/2000
JP    P2000-229072 A    8/2000

OTHER PUBLICATIONS

"Recommendation of Office 2000 Common Object Programming", [online], [retrieved on Feb. 28, 2003], Internet, <URL: http://www.moug.net/skillup/opm/opmSep.2001.htm>.

* cited by examiner

*Primary Examiner*—Max F. Hindenburg
*Assistant Examiner*—Michael Astorino
(74) *Attorney, Agent, or Firm*—McDermott Will & Emery LLP

(57) ABSTRACT

Disclosed is a health care system, comprising: a living body data input unit; a living body data display unit; and an advice display unit, wherein said living body data input unit enters the living body data, said living body data display unit displays the living body data, and said advice display unit displays an advice about health according to said living body data. Furthermore, said advice display unit displays the advice about health in such manner that a human animation character points to the advice within a balloon with a hand while moving a mouth and waving the hand.

7 Claims, 19 Drawing Sheets

FIG.12

| | | Reduction | | | No Change | Increase | | |
|---|---|---|---|---|---|---|---|---|
| | | 1% ≤ Body Weight <3%(suitable change) | 3% ≤ Body Weight <5%(slightly much reduction) | 5% ≤ Body Weight (too much reduction) | -1< Body Weight <+1 | 1% ≤ Body Weight <3%(suitable change) | 3% ≤ Body Weight <5%(slightly much increase) | 5% ≤ Body Weight (too much increase) |
| Slender | | Body weight has reduced. Correct diet can't be determined only depending on the change in body weight. | | | Body weight is maintained. Continue a habit to take exercise. | Body weight has increased. If body weight is increased, but body fat is reduced then it is considersd that amount of muscle may be increased. | | |
| Muscle Standard | | Body weight has reduced. It is best to continue the exercise without any over-burden,but take a rest when body condition is poor. | | | Body weight is maintained. Take a rest when body condition is poor. | Body weight has increased. Pay attention not to eat too much. | | |
| | | Body weight has reduced. Correct diet properly keeps body fat. | | | | | | |
| Adiposity Latent | | Body weight has reduced. Correct diet reduces not only body weight,but also body fat. | Body weight has reduced. Pay attention not to reduce body weight too much. | Body weight has reduced. Too much reduction of body weight affects your health. Pay attention. | | Body weight has gradually increased. Are you lacking of exercise ? | Body weight tends to increse. Are you lacking of exercise ? | Body weight has rapidly increased. Are you lacking of exercise ? |
| Adiposity Real | | Body weight has reduced. If you feel fatigue after exercise or even on the next day take a rest. | Body weight has reduced. Correct diet reduces not only body weight,but also body fat. | Body weight has reduced. Improvement in physical constitution increases your life quality. Reduce your body weight to the target of healthy body weight. | | Body weight has gradually increased. Tendency of adiposity is one of the factors for adult non-communicable disease. | Body weight tends to increase. Tendency of adiposity is one of the factors for adult non-communicable disease. | Body weight has rapidly increased. Pay attention. |

FIG.13

| | Increase |
|---|---|
| | 3%≦Body Weight＜5%(slightly much increase) |
| Latent Adiposity | Body weight tends to increase.<br>Are you lacking of exercise ? |
| | Body weight tends to increase.<br>Pay attention. |
| | Body weight tends to increse.<br>Examine your meal and exercise. |
| | Body weight tends to increase.<br>Do you have increased snack between meals ? |
| | Body weight has increased.<br>Examine a habit of your meals and exercise once again. |
| | Body weight has increased.<br>Correct diet reduces body weight together with body fat, but increases basal metabolism. |
| | Body weight tends to increased.<br>Examine your life style as soon as possible. |
| | Body weight has increased.<br>Adiposity may trigger any adult non-communicable disease.<br>Examine your life style as soon as possible |

HEALTH CARE SYSTEM

BACKGROUND OF THE INVENTION

1. Field of the Invention

The present invention relates to a health care system for controlling living body measurement data, and more particularly to, such health care system that prompts for a user to carefully watch an advice message for advising the user about health on the basis of the living body measurement data.

2. Prior Art

In the past, methods of prompting for a PC user to carefully watch a message on a PC screen have been known. One example of which is Microsoft Corporation, word processor software "WORD", Office Assistant Balloon Function (see non-patent document 1, for example). The balloon function acts to display a female animation character with a message in a balloon, as shown in FIG. 17.

Additionally, a patent application regarding a health care system has been filed by the same applicant as the present application in which living body measurement data is sent to a data server for storage, and thereafter, it is retrieved for advising users about their health individually (see patent document 1).

The reference documents associated with the present invention are as follows:

Non-Patent Document 1:

"Recommendation of Office 2000 Common Object Programming", [online], [retrieved on Feb. 28, 2003], Internet, <URL:http://www.moug.net/skillup/opm/opm09-01.htm>

Patent Document 1:

Japanese Patent Laid-Open No. 2000-229072

However, the female animation character has no action associated with the message within the balloon. Therefore, the balloon function simply plays a role of mascot in that it can only relieve any tension involved in the work of the user.

In view of the above it is an object of the present invention is to solve the prior art problems, as described above, and to provide a new and improved health care system that can prompt for a user to carefully watch an advice message for the health.

SUMMARY OF THE INVENTION

In order to attain such object the present invention provides a health care system, comprising: a living body data input unit; a living body data display unit; and an advice display unit, wherein said living body data input unit enters the living body data, said living body data display unit displays the living body data, said advice display unit displays an advice about health according to said living body data, and said advice display unit displays the advice about health in such manner that a human animation character points to the advice within a balloon with a hand while moving a mouth and waving the hand.

According to one embodiment of the present invention the health care system further comprises a living body data measurement unit and a receiver unit, said living body data measurement unit measures the living body data, said receiver receives the living body data from the living body data measurement unit, and said input unit acquires the living body data from the receiver.

According to another embodiment of the present invention said living body data measurement unit includes at least one of a body fat meter, a pedometer, and a sphygmomanometer.

According to further embodiment of the present invention if the body fat meter is used for the living body data measurement unit said living body data includes at least one of body weight, body fat rate, body fat mass, basal metabolism, total energy consumption and visceral fat level.

According to yet further embodiment of the present invention if the pedometer is used for the living body data measurement unit said living body data includes at least one of number of steps, distance, calorie consumption and amount of burned fat.

According to yet further embodiment of the present invention if the sphygmomanometer is used for the living body data measurement unit said living body data includes at least one of highest blood pressure, lowest blood pressure and pulse rate.

According to yet further embodiment of the present invention said receiver unit includes a wireless receiving section which is normally in standby condition and which, upon receiving the living body data from the living body data measurement unit, acts to check whether there is any problem in the data, and if no, to acquire the living body data.

According to yet further embodiment of the present invention if the advice is for diet it includes a precaution or a comment regarding at least one of body build, body weight, body fat mass and basal metabolism.

According to yet further embodiment of the present invention if the advice is for adult non-communicable disease it includes a precaution or a comment regarding at least one of body build, body weight, body fat mass and visceral fat level.

According to yet further embodiment of the present invention if the advice is for diet said advice display unit includes a graphic display unit for graphically displaying at least one of body weight, body fat mass, basal metabolism and total energy consumption.

According to yet further embodiment of the present invention if the advice is for adult non-communicable disease said advice display unit includes a graphic display unit for graphically displaying at least one of body weight, body fat mass, visceral fat level, highest blood pressure and lowest blood pressure.

In another aspect the present invention provides a health care system, comprising: a living body data measurement unit; a receiver unit; and a personal computer, wherein said living body data measurement unit measures living body data, said receiver unit receives the living body data from the living body data measurement unit, said personal computer is "USB" connected to the receiver unit, and said receiver unit includes a wireless receiving section which is normally in standby condition and which, upon receiving the living body data from the living body data measurement unit, acts to check whether there is any problem in the data, and if no, to acquire the living body data.

According to one embodiment of the present invention said receiver receives the living body data from the living body data measurement unit via electromagnetic wave or infrared ray.

According to another embodiment of the present invention said living body data measurement unit includes at least one of a body fat meter, a pedometer, and a sphygmomanometer.

According to further embodiment of the present invention if the body fat meter is used for the living body data measurement unit said living body data includes at least one of body weight, body fat rate, body fat mass, basal metabolism, total energy consumption and visceral fat level.

According to yet further embodiment of the present invention if the pedometer is used for the living body data measurement unit said living body data includes at least one of number of steps, distance, calorie consumption and amount of burned fat.

According to yet further embodiment of the present invention if the sphygmomanometer is used for the living body data measurement unit said living body data includes at least one of highest blood pressure, lowest blood pressure and pulse rate.

According to yet further embodiment of the present invention if the body fat meter or the sphygmomanometer is used for the living body data measurement unit it sends the living body data to the receiver unit in frame synchronized manner upon depressing a data transmission button after measurement is done.

According to yet further embodiment of the present invention if the pedometer is used for the living body data measurement unit, upon placing the pedometer including a reed switch on the receiver unit including a permanent magnet, then the reed switch is turned ON so that the pedometer sends the living body data to the receiver unit in stepping manner.

BRIEF DESCRIPTION OF THE DRAWINGS

Now, the present invention will be described in more detail with reference to the accompanying drawings, in which:

FIG. 12 is a table listing advice messages for body weight;

FIG. 13 is another table listing advice messages for body weight;

DESCRIPTION OF THE PREFERRED EMBODIMENTS

Figure 1:
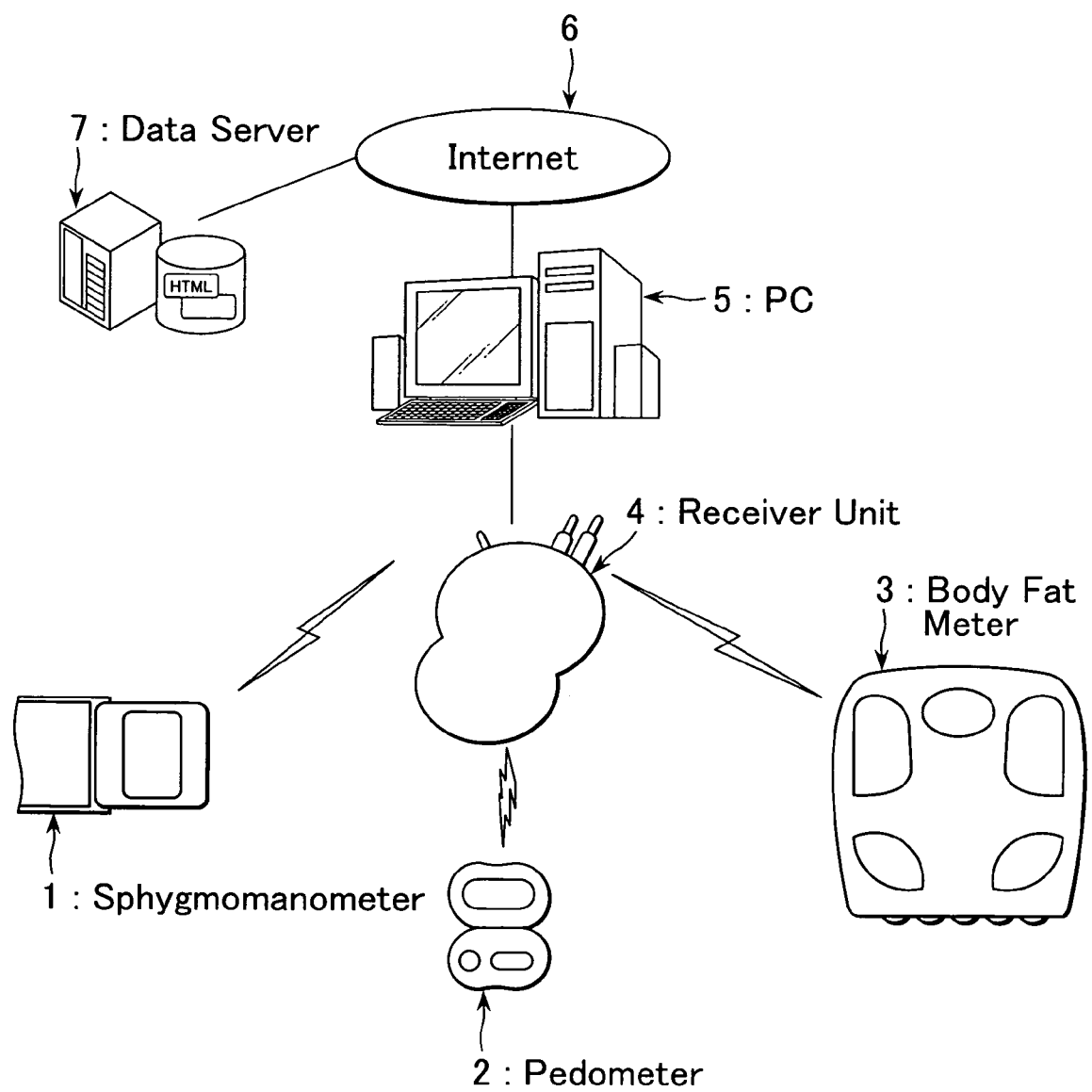
FIG. 1 is a view illustrating one embodiment of a health care system according to the present invention.

Referring to FIG. 1, one embodiment of a health care system according to the present invention is shown. The health care system includes a sphygmomanometer 1 for measuring the blood pressure, a pedometer 2, a body fat meter 3, a receiver unit 4 for receiving measurement data from the instruments 1, 2, 3 via electromagnetic wave or infrared ray communication, a personal computer (hereafter referred to as "PC") 5 that is "USB" connected to the receiver unit 4, and a data server 7 connected to the PC 5 via an Internet 6.

The sphygmomanometer 1 is the prior art instrument, except that it has capability of wireless data transmission, and therefore, further description of the sphygmomanometer 1 with reference to e.g. an internal block diagram is omitted here. The pedometer 2 is the prior art device, except that it has infrared data transmission function, and therefore, further description of the pedometer 2 is omitted here. In the same manner, the body fat meter 3 is the prior art instrument, except that it has capability of wireless data transmission, and therefore, further description is omitted here.

Figure 2:
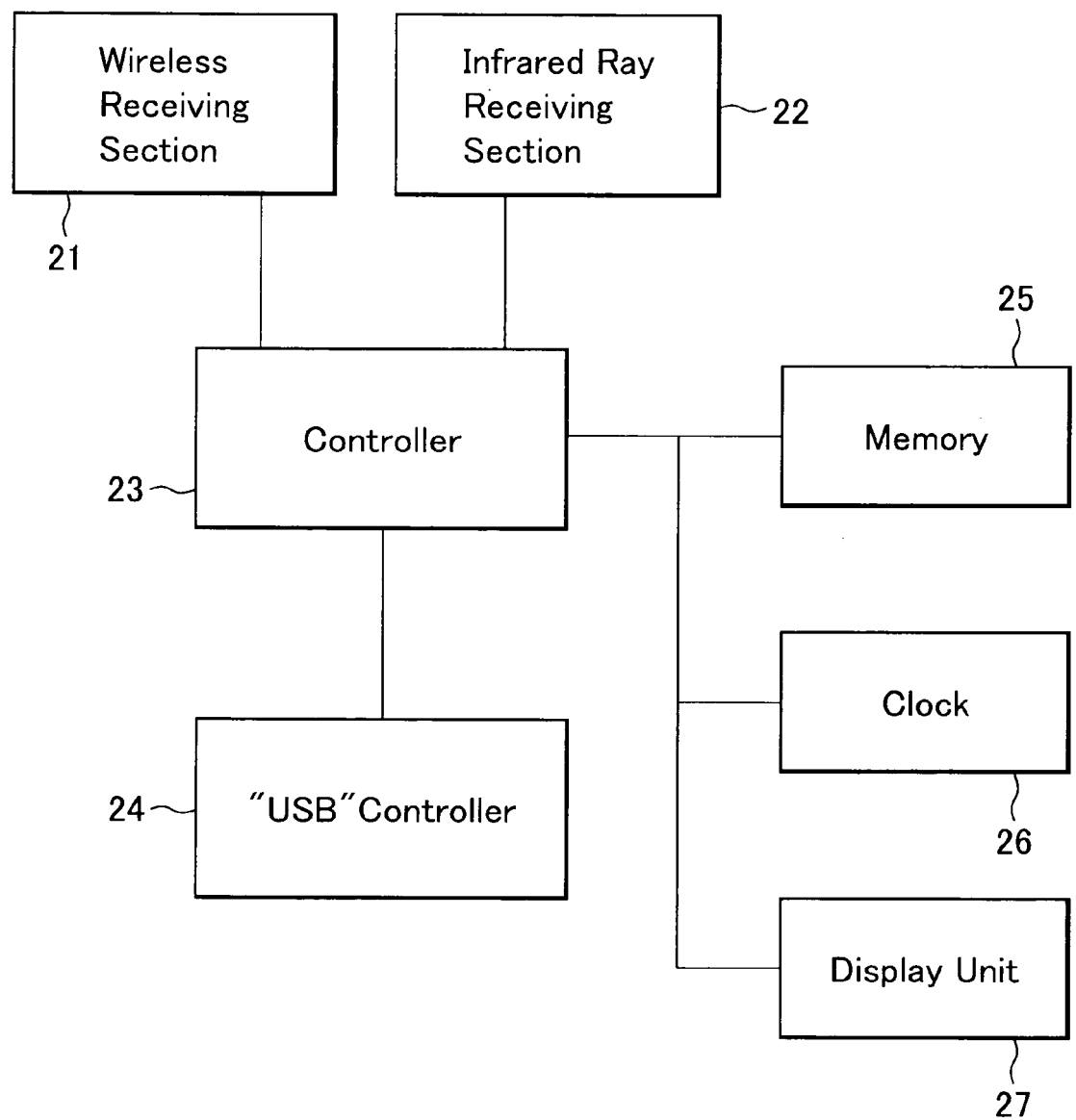
FIG. 2 is a logic block diagram of a receiver unit.

Referring to FIG. 2 the receiver unit 4 is shown in logic block diagram. The receiver unit 4 includes a wireless receiving section 21 for receiving the data sent from the sphygmomanometer 1 or the body fat meter 3, an infrared ray receiving section 22 for receiving the data sent from the pedometer 2, a memory 25, a clock 26, a display unit 27, a controller 23 for controlling other circuit blocks, and a "USB" controller 24 for controlling the "USB".

The PC 5 is the prior art personal computer, except that it has capability of reception from the receiver 4 via a "USB" connection. The PC 5 executes a health care program which acts to manage measurement data of the sphygmomanometer 1, the pedometer 2 and the body fat meter 3, to graphically display any change in measurement data with the time in a day, and to display some advice messages about diet or adult non-communicable disease. The detailed description of the health care program will be made in latter.

The data server 7 includes prior art file and WEB servers, as described in Japanese Patent Laid-Open No. 2000-229072, to which the data as managed under the health care program is partially sent from the PC5. Based on the data stored in the data server 7, a physician, a nutritionist or an exercise instructor advises the users individually about how to improve the health condition in real time via an Internet.

Now, an operation of the health care system according to the present invention will be described with reference to the accompanying drawings. First of all, transmission/reception of the data between the sphygmomanometer 1 or the body fat meter 3 and the receiver unit 4 will be described. When measurement is done with the instrument such as the sphygmomanometer or the body fat meter and a data transmission button on each instrument is depressed then a transmission section of the instrument sends the measurement data to the receiver unit 4 in frame-synchronized manner. The wireless receiving section 21 of the receiver unit 4 is normally in standby condition, and as soon as the data is received, it starts to check whether there is any problem in the data or not. If not, the data is acquired by the receiver unit.

Accordingly, simply by depressing the data transmission button on the instrument such as the sphygmomanometer 1 or the body fat meter 3 after measurement is done, the measurement data can be sent to the receiver unit 4 which is away from the instrument by some distance so that the receiver unit can automatically acquire the measurement data. There is no need that after depressing the data transmission button an operator purposely goes to the position where the receiver unit 4 is located and depresses a reception button thereon. It is useful in that there is less labor required for the user to acquire the measurement data.

Figure 18:
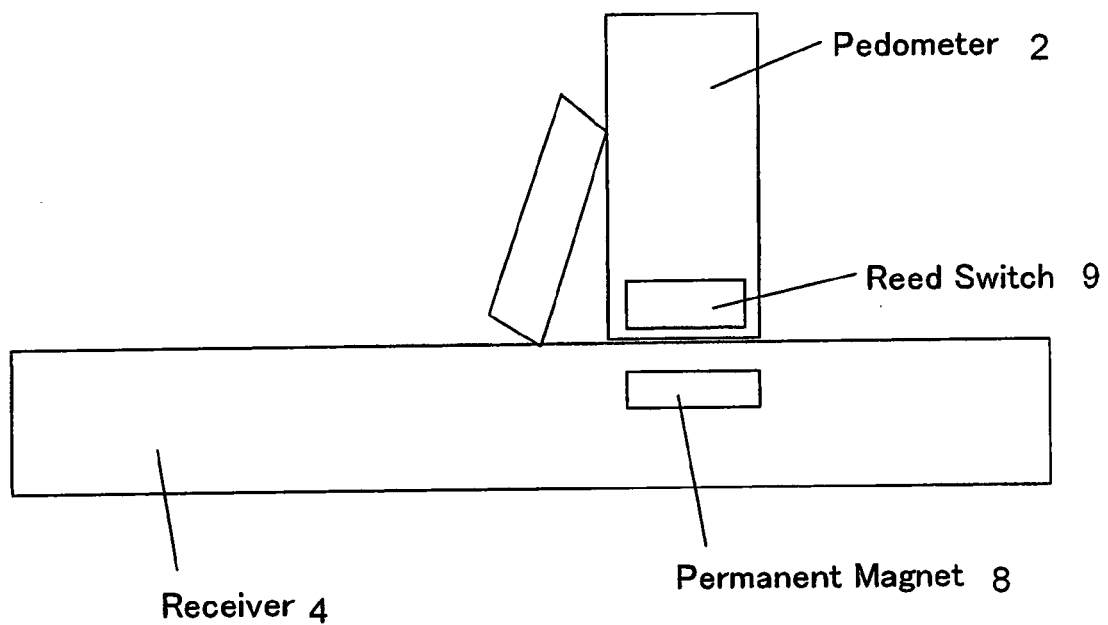
FIG. 18 illustrates the pedometer of FIG. 1 on the receiver unit of FIG. 1.
Figure 19A:
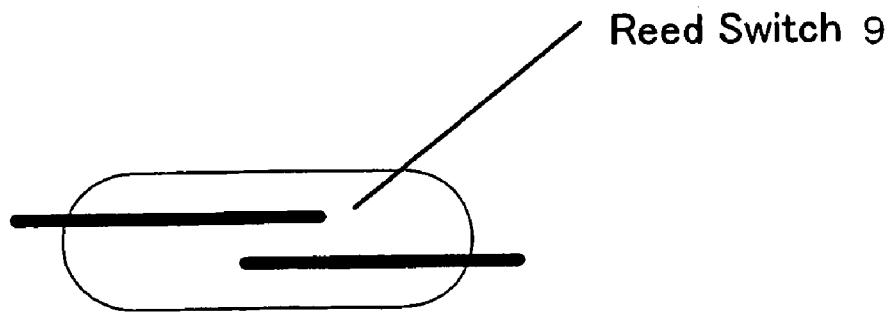
FIGS. 19(*a*) and 19(*b*) illustrate a reed switch of the pedometer of FIG. 1.
Figure 19B:
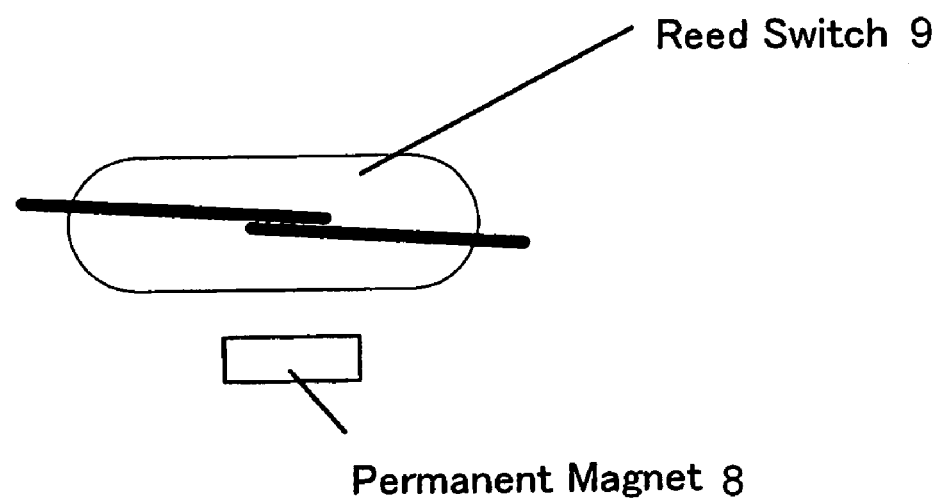

Next, transmission/reception of the data between the pedometer 2 and the receiver unit 4 will be described. As shown in FIG. 18, a permanent magnet 8 is mounted on the receiver 4 and a reed switch 9, as shown in FIG. 19(a), is mounted on the pedometer 2 so that when the pedometer 2 is placed on the receiver unit 4 the reed switch 9 is turned ON, as shown in FIG. 19(b), whereby the pedometer 2 sends the measurement data to the receiver unit 4 in stepping manner. The infrared receiving section 22 of the receiver unit 4 receives the measurement data from the pedometer 2.

Accordingly, simply by placing the pedometer 2 on the receiver unit 4 after measurement is done with the pedometer 2, the receiver unit 4 can acquire the measurement data. Therefore, there is less labor required for the user to acquire the measurement data. In contrast thereto, if a "USB" cable is used for physical and direct connection between the pedometer 2 and the PC 5 without the receiver unit 4 so that the PC 5 receives the data from the pedometer 2 then it is significantly tedious and time consuming for the user to connect the "USB" cable to "USB" terminals on the pedometer.

Figure 3:
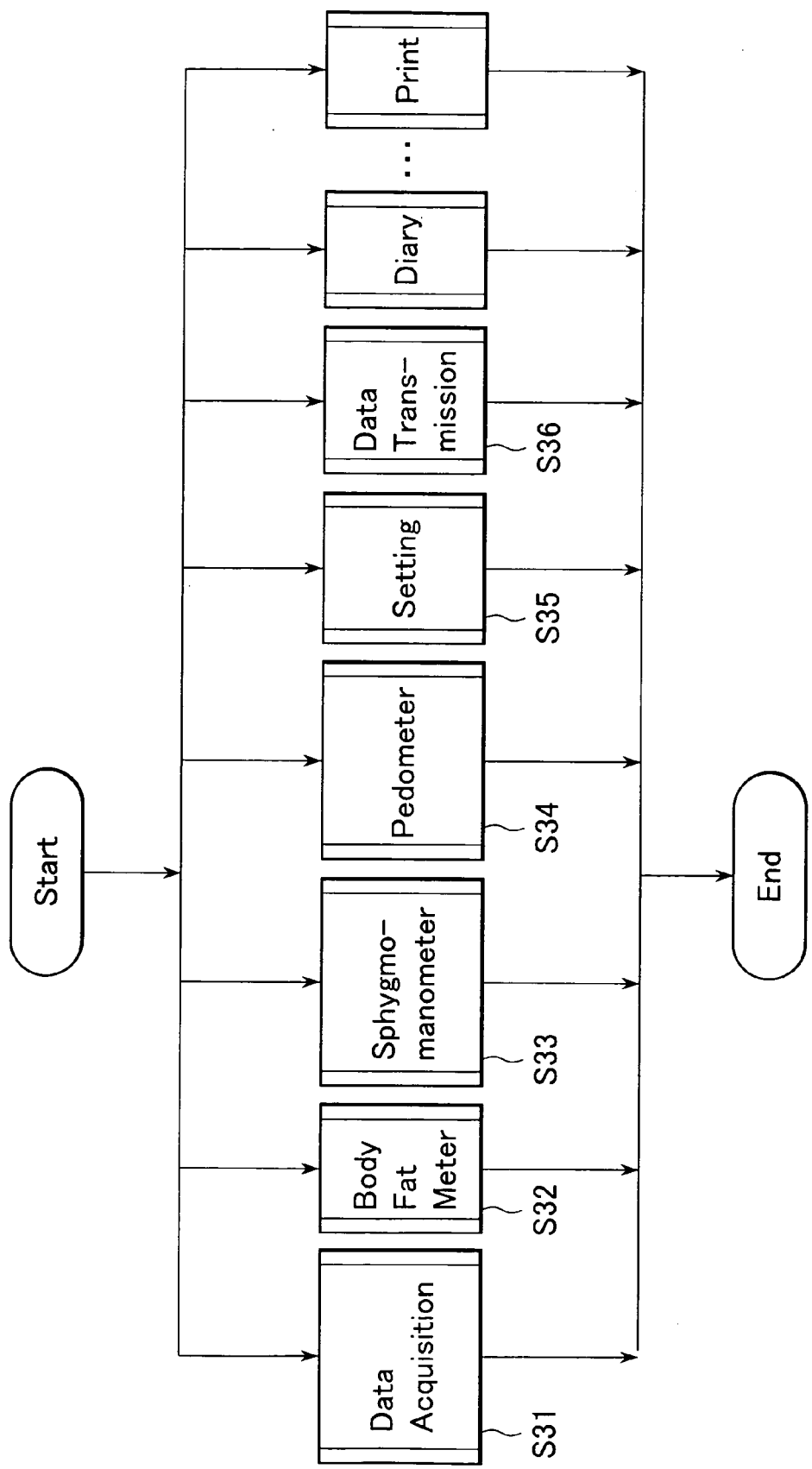
FIG. 3 is a flow chart illustrating a main routine of a health care program.
Figure 4:
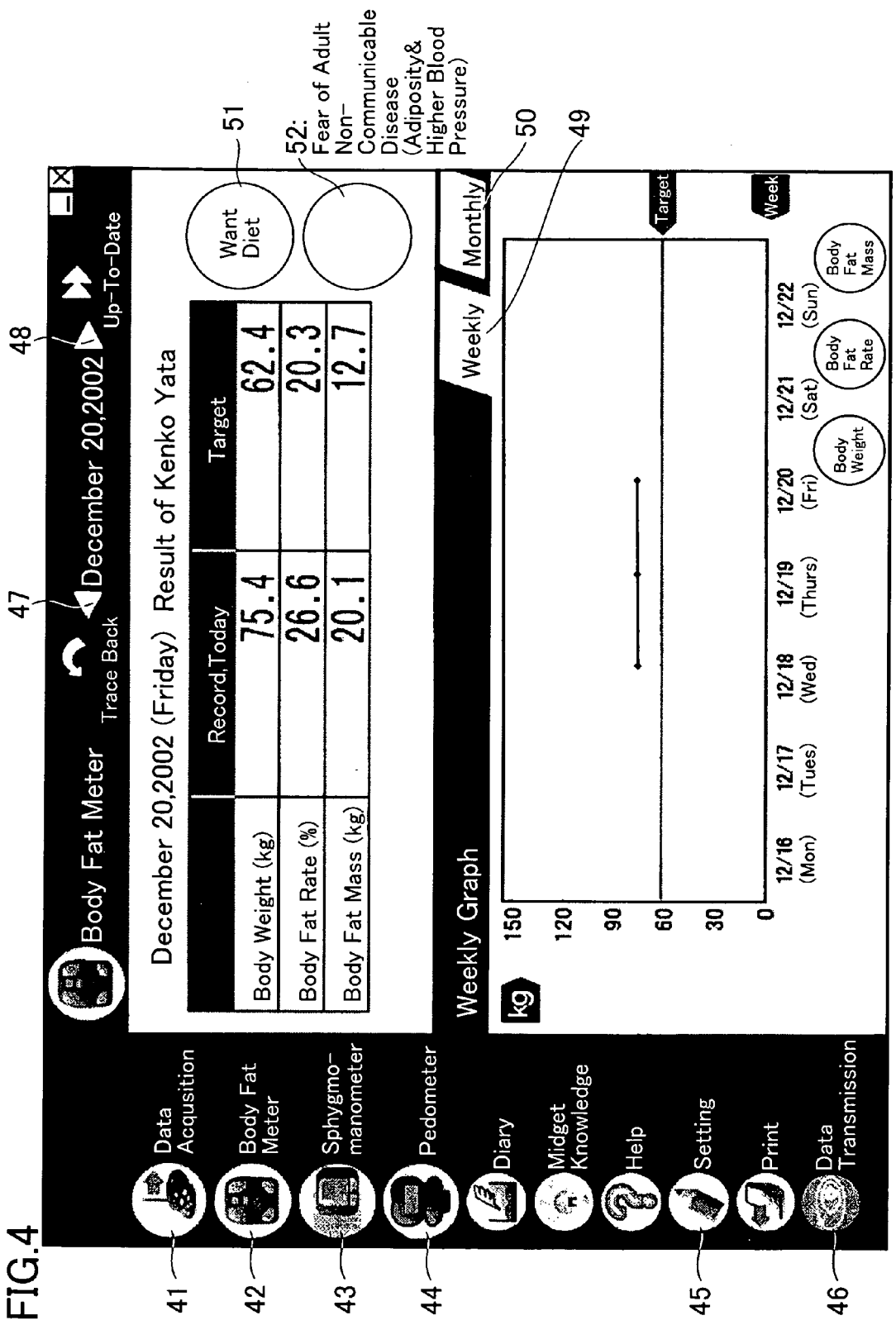
FIG. 4 is a view of display screen showing measurement data of a body fat meter.

Next, an operation of the health care program running in the PC 5 will be described. FIG. 3 is a flow chart illustrating a main routine of the health care program. When the main routine is activated the PC5 initially displays predetermined items on the display screen, as shown in FIG. 4. Menu buttons for the health care program such as "Data Acquisition", "Body Fat Meter", . . . and "Data Transmission" are shown in the left-hand side of FIG. 4. When a mouse is clicked on the "Data Acquisition" button 41 the measurement data is acquired into the PC 5 from the receiver unit 4, at step S31. In particular, the measurement data from the body fat meter includes body weight, body fat rate, body fat mass, basal metabolism, total energy consumption, and visceral fat level (i.e., the level of visceral fat mass calculated from visceral fat area). The measurement data from the sphygmomanometer includes the highest blood pressure, the lowest blood pressure and pulse rate. The measurement data from the pedometer includes the number of steps, distance, calorie consumption, and amount of burned fat. Then, the mouse is clicked on the "Body Fat Meter" button 42 to proceed to step S32 wherein a body fat meter routine is executed, which will be described in latter.

Thereafter, the mouse is clicked on a "Blood Pressure" button 43 to proceed to step S33 wherein a sphygmomanometer routine is executed. Next, when the mouse is clicked on a "Pedometer" button 44, a pedometer routine is executed at step S34. Then, when a "Setting" button 45 is depressed, various kinds of settings for the health care program are performed at step S35. Then, the mouse is clicked on the "Data Transmission" button 46 to proceed to step S36 wherein the measurement data is sent to the data server 7.

Figure 5:
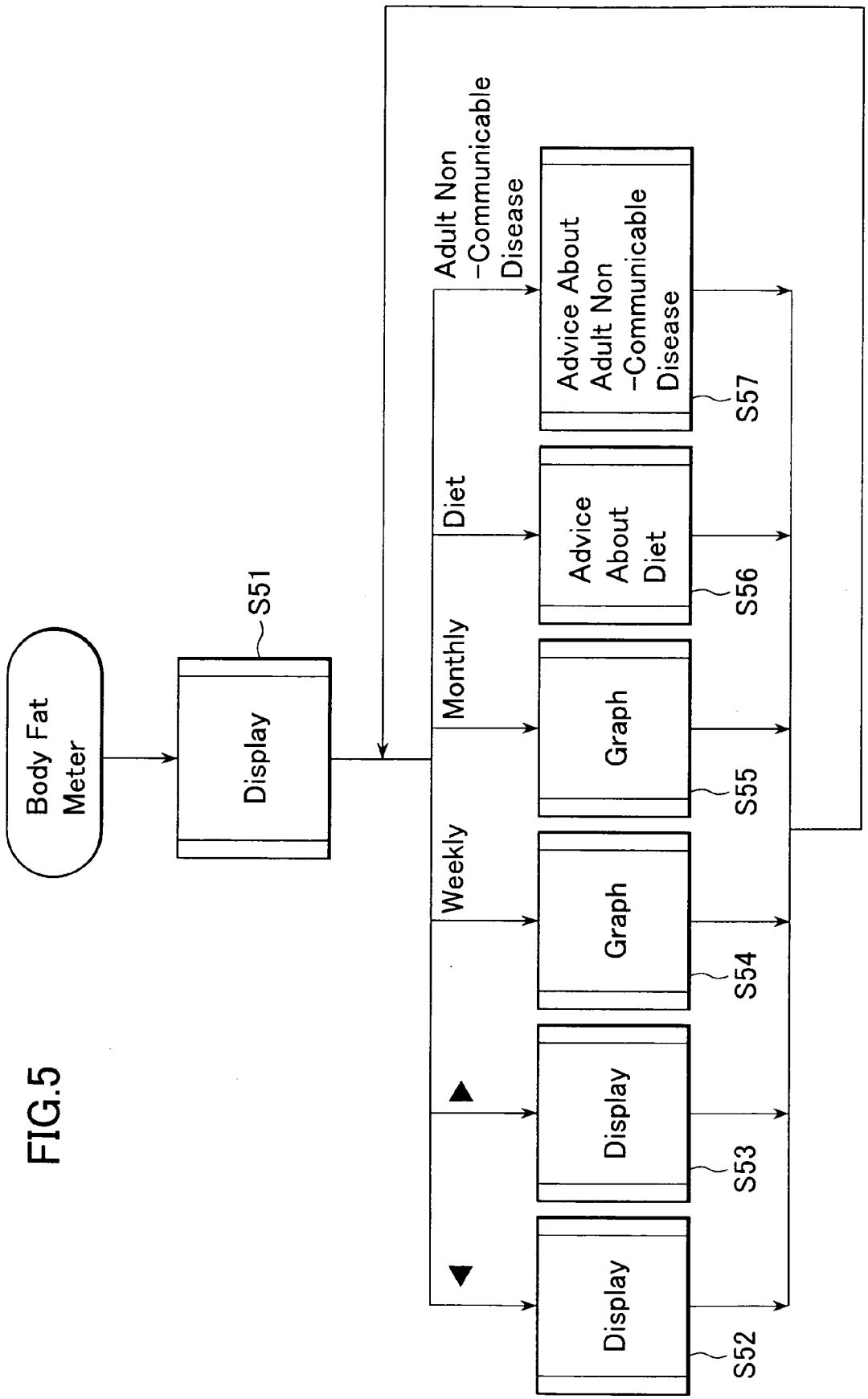
FIG. 5 is a flow chart illustrating an operation of a body fat meter routine.

Referring to a flow chart of FIG. 5, an operation of the body fat meter routine will be described. At step S51 a display routine is executed to display the data of body weight, body fat rate and body fat mass as measured on that day when the health care program is executed as well as the corresponding target values, at an upper portion of the screen, as shown in FIG. 4. In addition, a graph of the body weight in that week is displayed at a lower portion of the screen.

If the mouse is clicked on a trianglar button 47 directed toward left hand side then the date displayed is traced back by one day and the measurement data on that day is displayed at step S52. On the other hand, if the mouse is clicked on a triangular button 48 directed toward right hand side then the date displayed is proceeded forwardly by one day and the measurement data on that day is displayed at step S53.

If the mouse is clicked on a "Week" button 49 the body weight in that week is displayed at step S54. Furthermore, if the mouse is clicked on a "Month" button 50 the body weight in that month is displayed at step S55.

If the mouse is clicked on a "Diet" button 51 then a diet advice routine is executed for advising about diet at step S56, which is described in latter. In addition, if mouse is clicked on an "adult non-communicable disease" button 52 then an adult non-communicable disease routine is executed for advising about adult non-communicable disease at step S57, which is described in latter.

Figure 6:
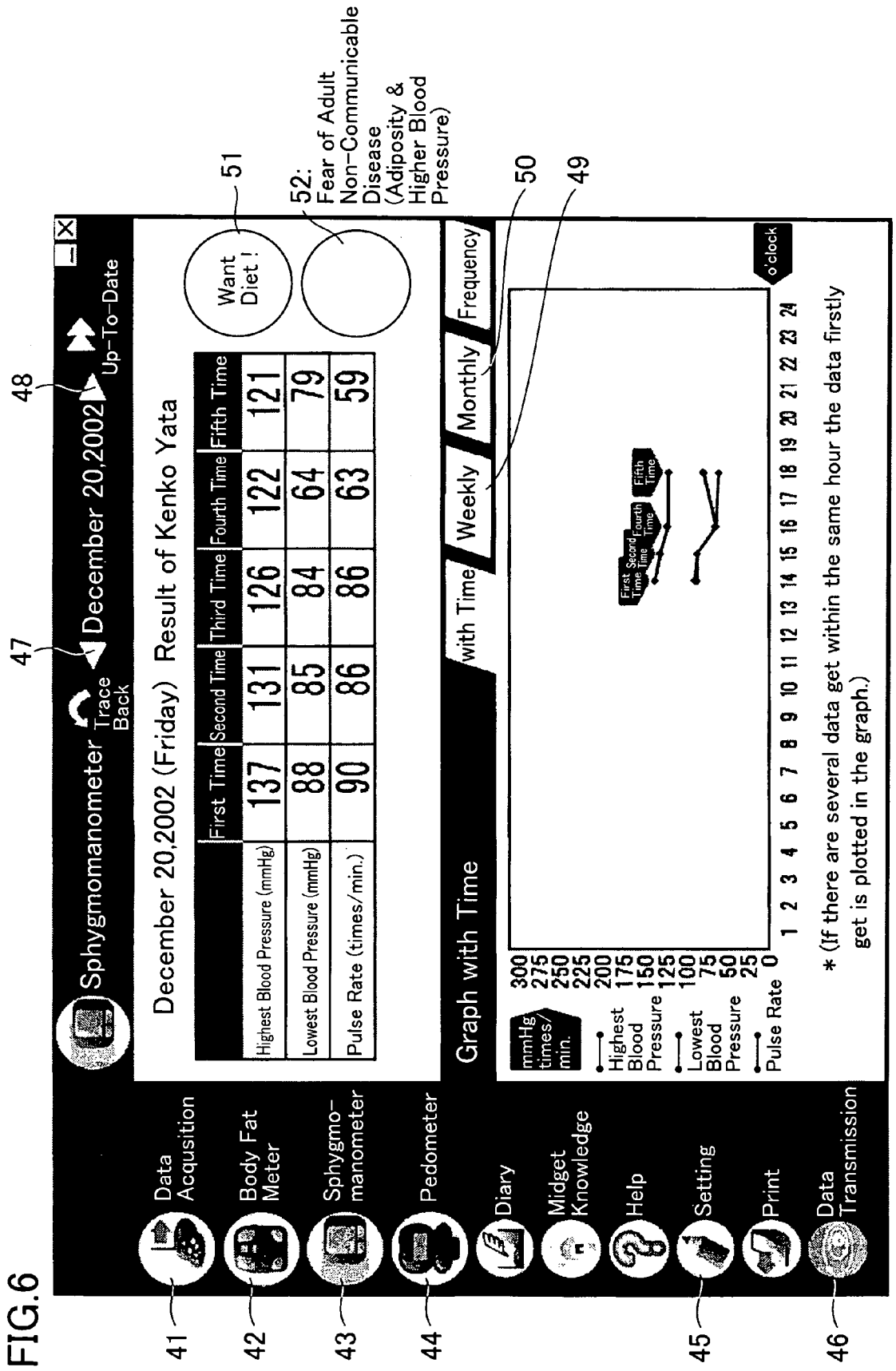
FIG. 6 is a view of display screen showing measurement data of a sphygmomanometer.
Figure 7:
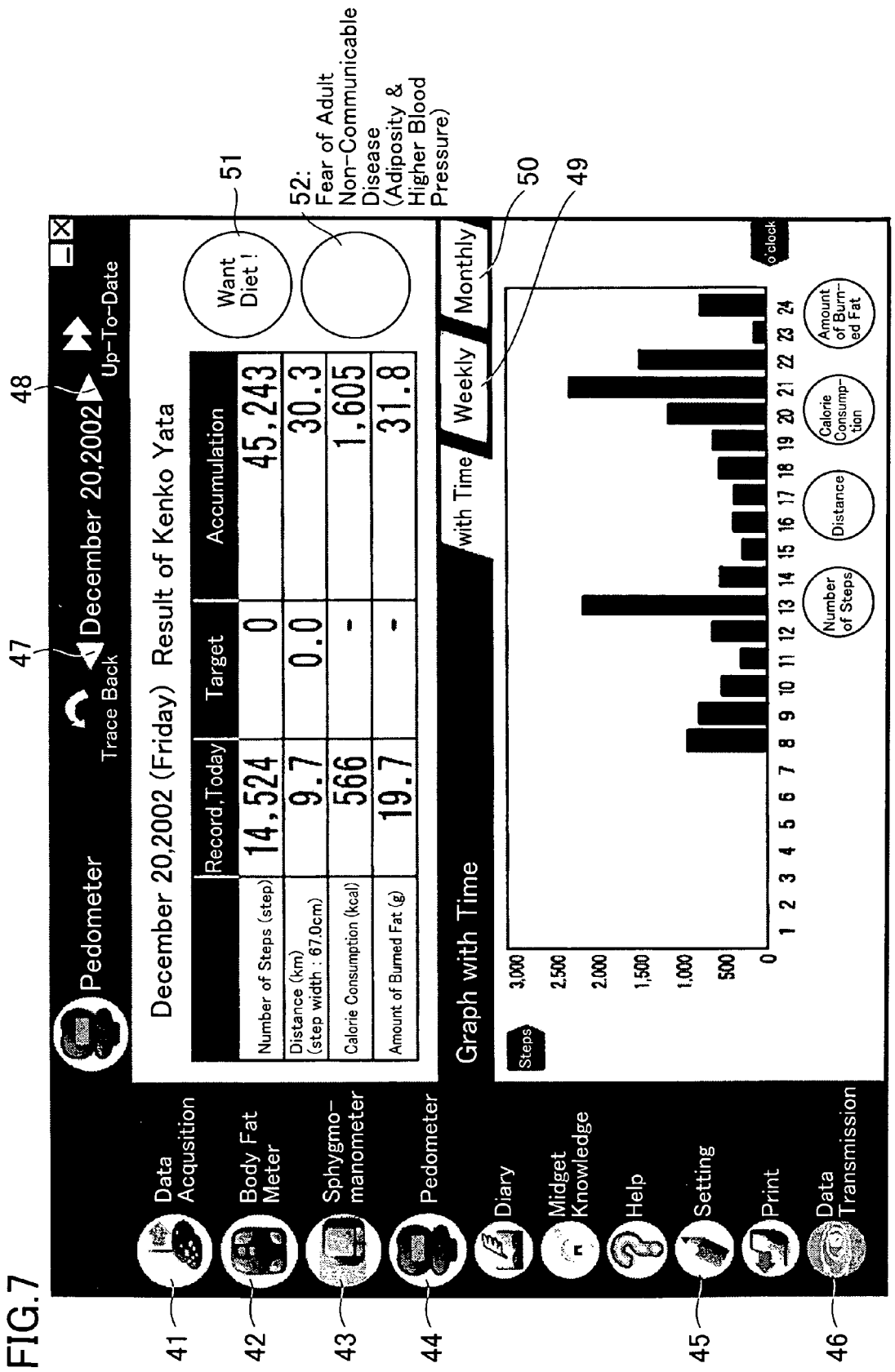
FIG. 7 is a view of display screen showing measurement data of a pedometer.

The sphygmomanometer routine and the pedometer routine are functionally equal to the body fat meter routine, except that the blood pressure or the number of steps is displayed. Accordingly, the results of execution of the sphygmomanometer routine and the pedometer routine are only shown in FIGS. 6 and 7, respectively. Any further description of the sphygmomanometer routine and the pedometer routine is omitted here.

Figure 8:
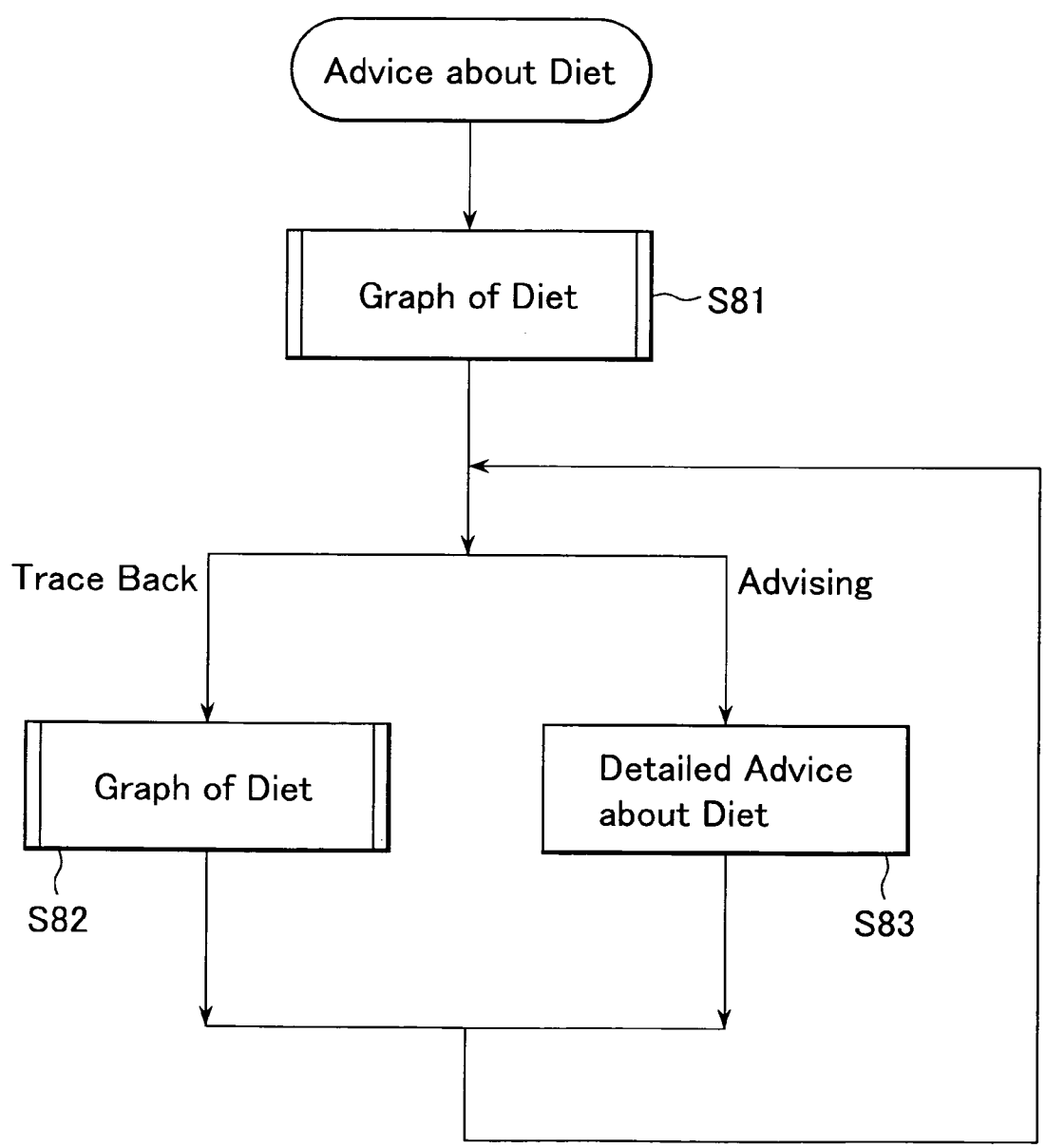
FIG. 8 is a flow chart illustrating an operation of diet advice routine.
Figure 9:
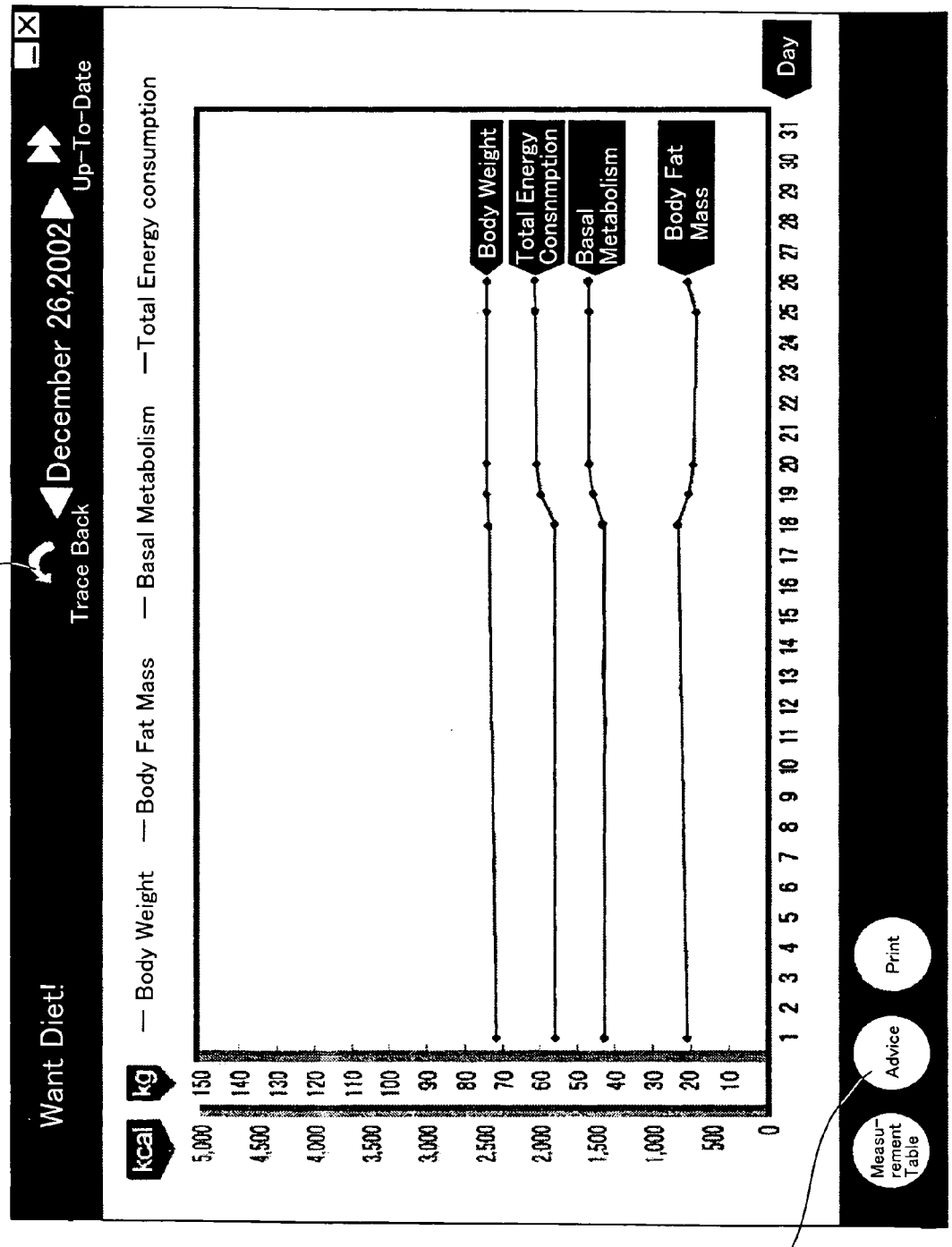
FIG. 9 is a view of display screen showing a diet graph.

Referring to FIG. 8, an operation of the diet advice routine will be described. At step S81 a diet graph routine is invoked so that a diet graph for that month is displayed on the PC screen, as shown in FIG. 9. The diet graph illustrates the body weight, body fat mass, basal metabolism and total energy consumption, all associated with diet. If the mouse is clicked on a "Trace Back" button 91 then the diet graph for the month assigned is displayed on the PC screen at step S82.

Figure 10:
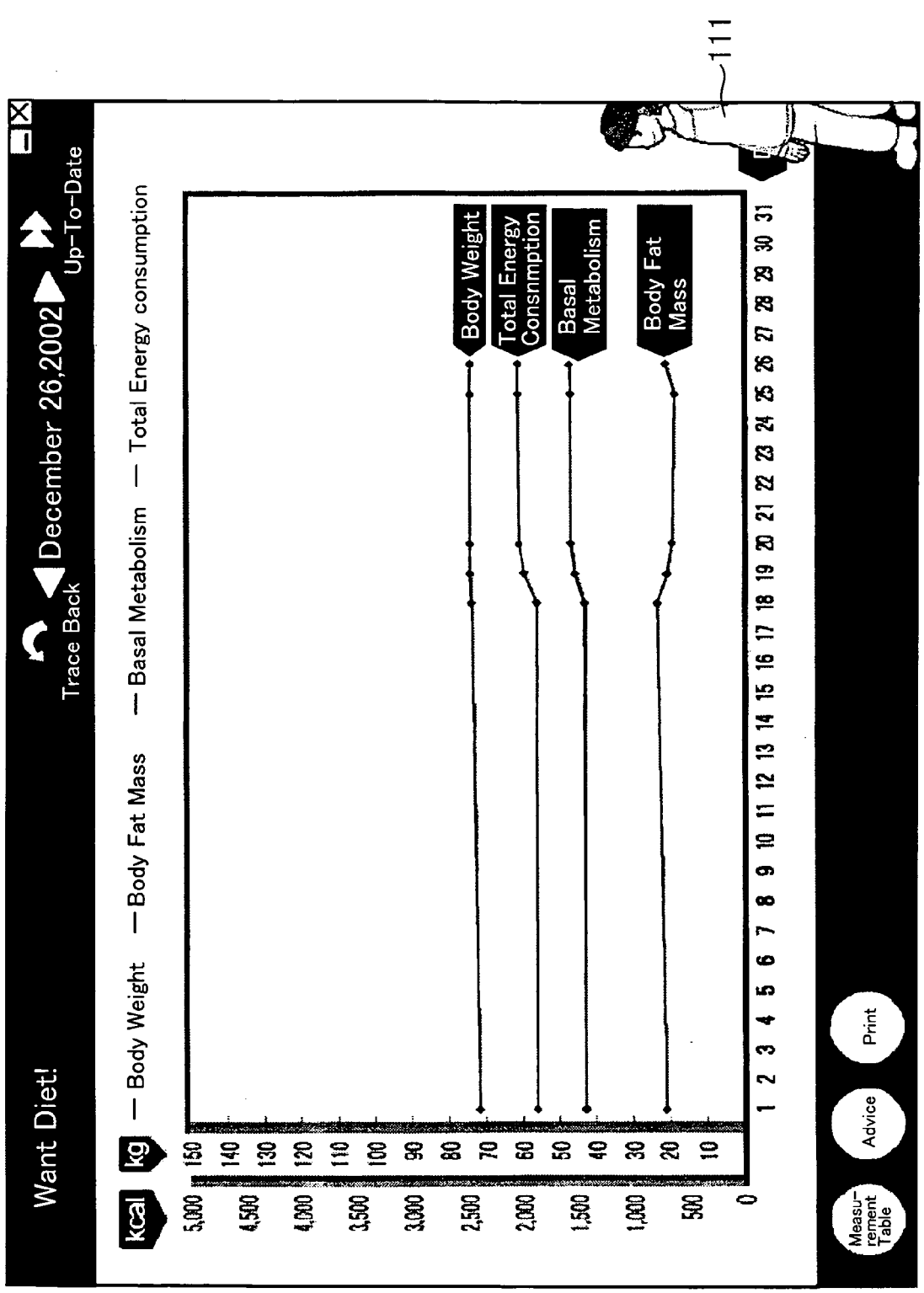
FIG. 10 is a view of display screen after a mouse is clicked on a diet advice button.
Figure 11:
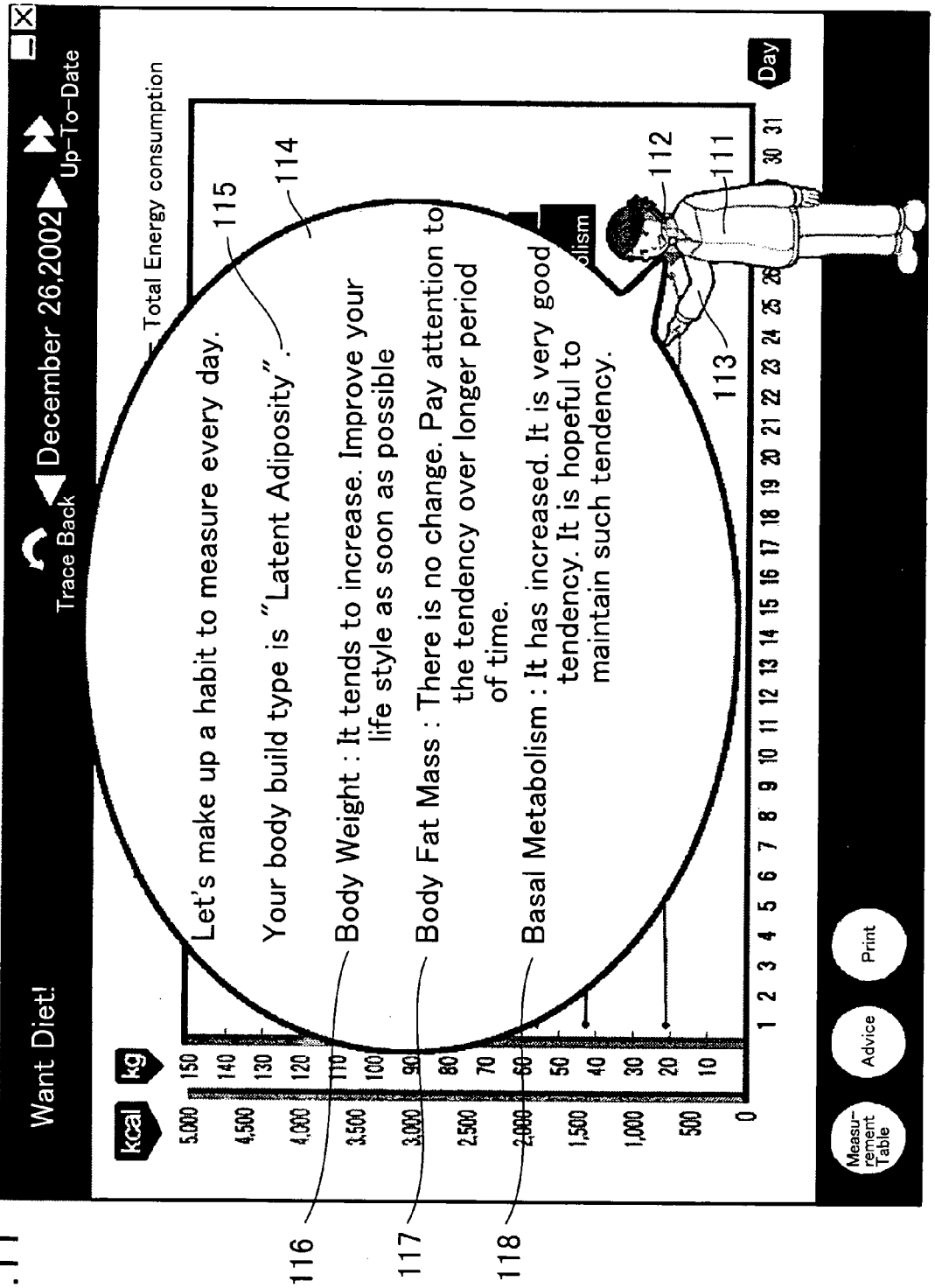
FIG. 11 is a view of display screen showing an advice message for diet.

If the mouse is clicked on the advice button 92 in FIG. 9 then the process of displaying the detailed advice message about diet is carried out at step S83. Initially, as shown in FIG. 10, an animation female character 111 appears on the screen from the right-hand side thereof while walking. Then, the animation female character 111 stops at the position on the screen, as shown in FIG. 11, and moves her mouth 112 and waves her hand 113 while pointing to a balloon 114 with her hand in which any precaution or comment for the body build, body weight, body fat mass and basal metabolism of a person under test is included. With the aid of movement of the mouth and the hand of the animation character the person who watches the screen would be under illusion as if an adviser gives an advice, and therefore, the person is prompted to carefully watch and understand the advice message.

Method of determining what precaution or comment is to be included in the balloon 114 for the body build, body weight, body fat mass and basal metabolism will be described hereafter. The body build 115 is selected among various types including slender, standard, muscle, latent adiposity and real adiposity based on "BMI" (Body Mass Index) and body fat rate.

Referring to FIG. 12, the precaution or comment for body weight 116 is issued according to the body build and the weight reduction or increase: weight reduction between not less than 1% and less than 3%; weight reduction between not less than 3% and less than 5%; weight reduction of not less than 5%; no weight change or weight between −1% and 1%; weight increase between not less than 1% and less than 3%; weight increase between not less than 3% and less than 5%; weight increase of not less than 5%. Although three types of message are provided at the maximum for each class of weight reduction, no weight change and weight increase in FIG. 12, four or more types of message may be provided in actual case. The message issued for the case of weight increase between not less than 3% and less than 5% and of body build of latent adiposity is illustrated in FIG. 13 by way of an example.

The precaution or comment for the body fat mass and basal metabolism is provided in the same manner as that of the body weight, as described above. Accordingly, further description of the message for the body fat mass and basal metabolism is omitted.

Figure 14:
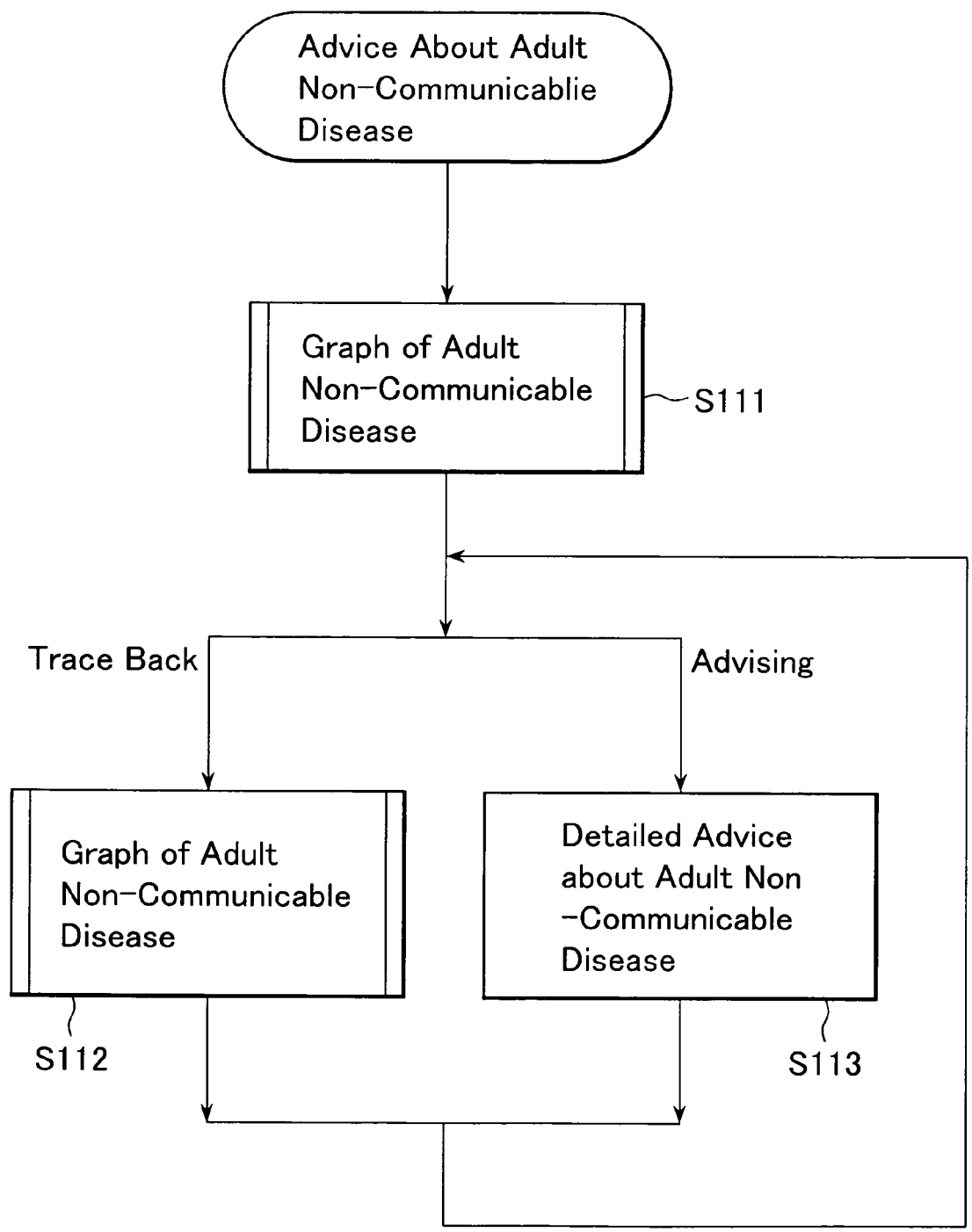
FIG. 14 is a flow chart illustrating an operation of adult non-communicable disease advice routine.
Figure 15:
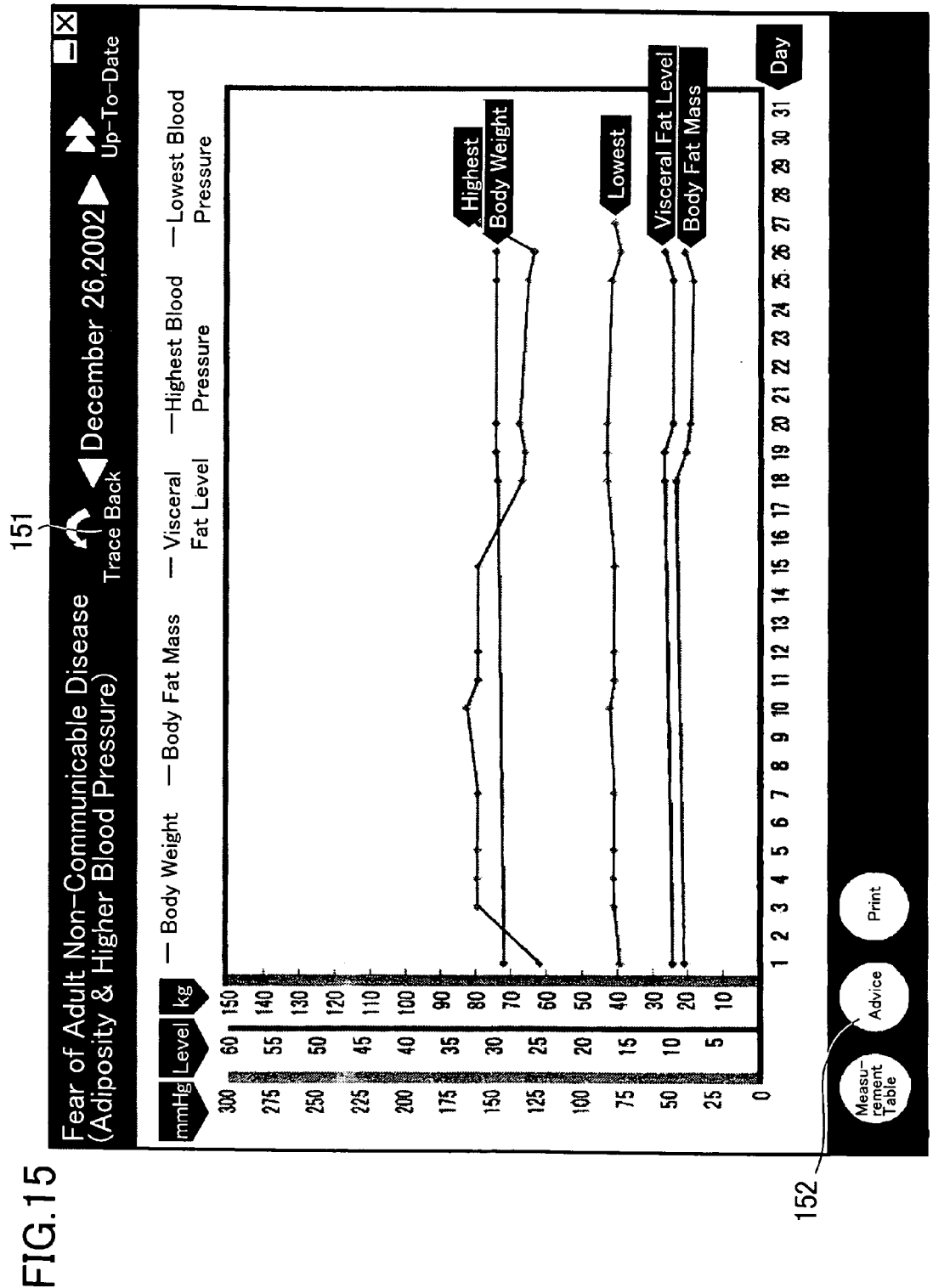
FIG. 15 is a view of display screen showing adult non-communicable disease graph.

Referring to FIG. 14, an operation of adult non-communicable disease advice routine will be described hereafter. At step S111 an adult non-communicable disease graph routine is invoked so that an adult non-communicable disease graph for that month is displayed on the PC screen, as shown in FIG. 15. The adult non-communicable disease graph illustrates the body weight, body fat mass, visceral fat level, highest blood pressure, and lowest blood pressure, all associated with adult non-communicable disease. If the mouse is clicked on a "Trace Back" button 151 then the adult non-communicable disease graph for the month assigned is displayed on the PC screen at step S112.

Figure 16:
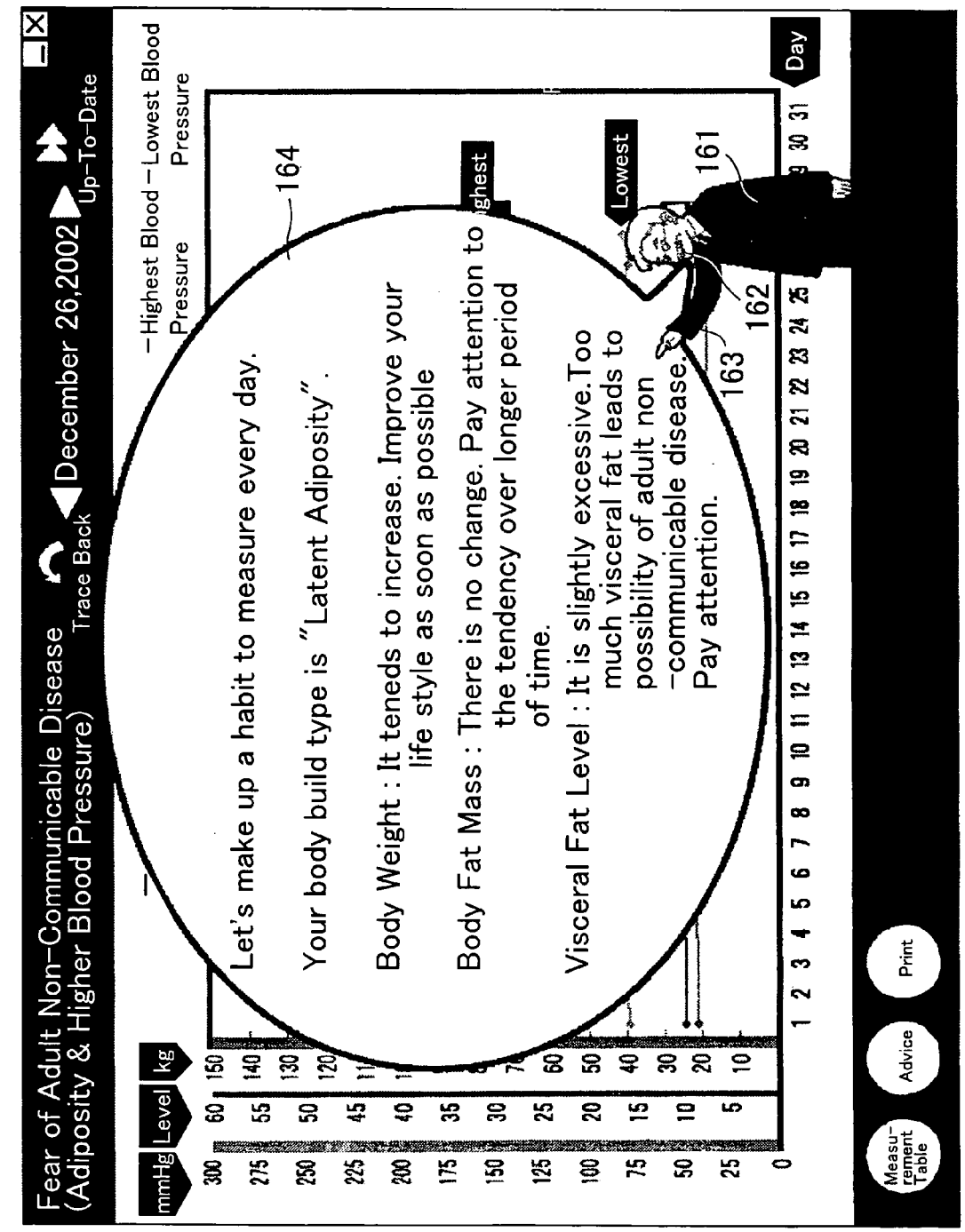
FIG. 16 is a view of display screen showing an advice message for adult non-communicable disease.
Figure 17:
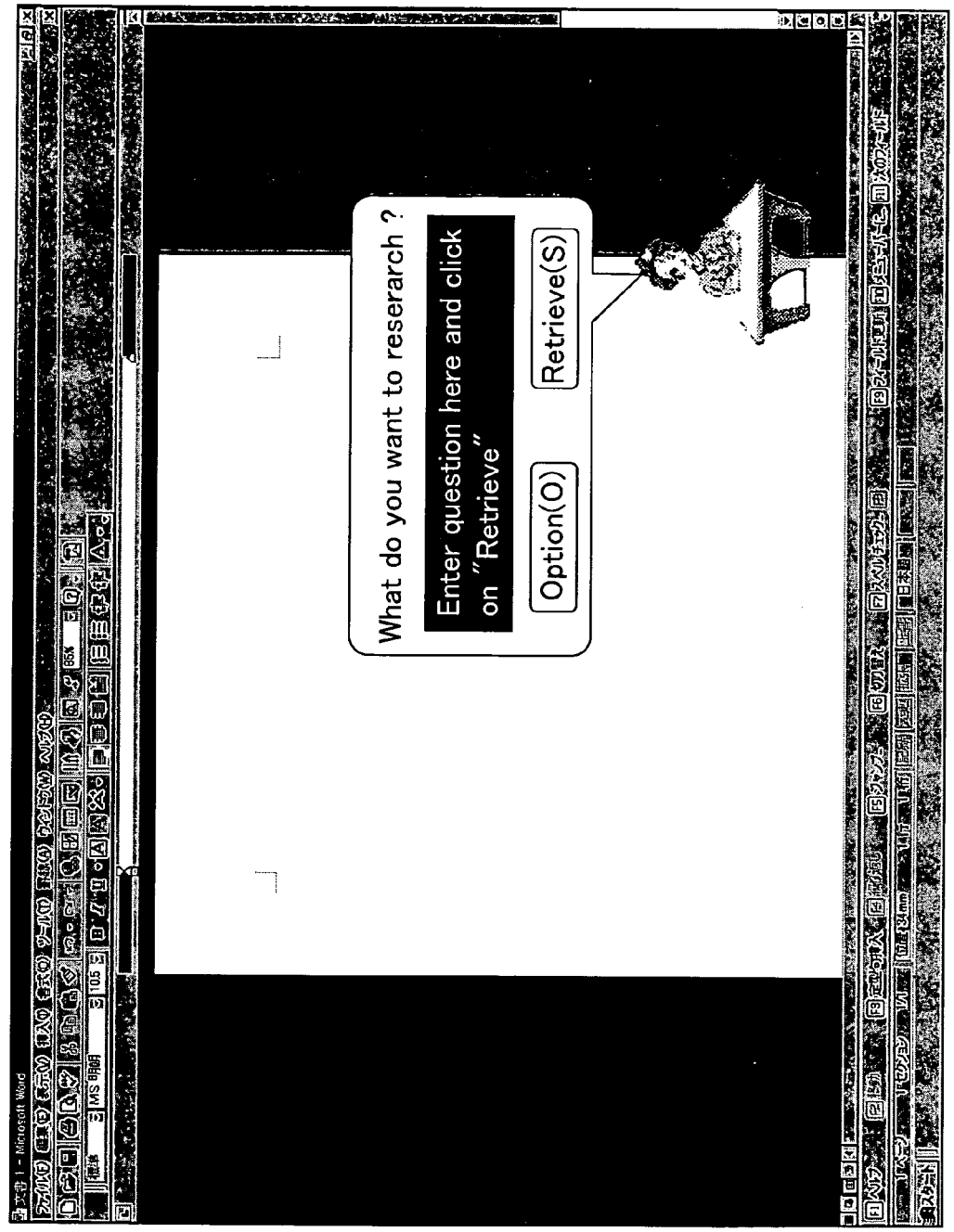
FIG. 17 is a view illustrating an Office Assistant Balloon function.

If the mouse is clicked on the advice button 152 in FIG. 15 then the process of displaying the detailed advice message about adult non-communicable disease is carried out at step S113. Initially, an animation male character appears on the screen from the right-hand side thereof while walking. Then, the animation male character 161 stops at the position on the screen, as shown in FIG. 16, and moves his mouth 162 and waves his hand 163 while pointing to a balloon 164 with his hand in which any precaution or comment for the body build, body weight, body fat mass and visceral fat level of a person under test is included. With the aid of movement of the mouth and the hand of the animation character the person who watches the screen is prompted to carefully watch and understand the advice message, as in the case of the advice about diet, as described above.

Method of determining what precaution or comment is to be included in the balloon 164 for the body build, body weight, body fat mass and visceral fat level is same as that of the advice about diet, as described above. Accordingly, further description is omitted here.

It is apparent from the foregoing that a health care system according to the present invention comprises: a living body data input unit; a living body data display unit; and an advice display unit, wherein said living body data input unit enters the living body data, said living body data display unit displays the living body data, said advice display unit displays an advice about health according to said living body data, and said advice display unit displays the advice about health in such manner that a human animation character points to the advice within a balloon with a hand while moving a mouth and waving the hand. Accordingly, a user is prompted to pay attention to the advice for understanding the progress and current state of the health data, which is extremely useful for motivation of self care of body condition (or precaution against any disease) in such manner that the use pays effort to improve his life style as earlier as possible by himself, for example.

A health care system according to the present invention comprises: a living body data measurement unit; a receiver unit; and a personal computer, wherein said living body data measurement unit measures living body data, said receiver unit receives the living body data, said personal computer is "USB" connected to the receiver unit, and said receiver unit includes a wireless receiving section which is normally in standby condition and which, upon receiving the living body data from the living body data measurement unit, acts to check whether there is any problem in the data, and if no, to acquire the living body data. Accordingly, simply by depressing the data transmission button on the instrument such as the sphygmomanometer 1 or the body fat meter 3 after measurement is done, the measurement data can be sent to the receiver unit 4 which is away from the instrument by some distance so that the receiver unit can automatically acquire the measurement data. There is no need that after depressing the data transmission button an operator purposely goes to the position where the receiver unit 4 is located and depresses a reception button thereon. It is useful in that there is less labor required for the user to acquire the measurement data.

In case where a pedometer is used for the living body data measurement unit, upon placing the pedometer including a reed switch on the receiver unit including a permanent magnet, then the reed switch is turned ON so that the pedometer 2 sends the living body data to the receiver unit 4 in stepping manner. Accordingly, simply by placing the pedometer 2 on the receiver unit 4 after measurement is done with the pedometer 2, the receiver unit 4 can acquire the measurement data. Therefore, there is less labor required for the user to acquire the measurement data. In contrast thereto, if a "USB" cable is used for physical and direct connection between the pedometer 2 and the PC 5 without the receiver so that the PC 5 unit receives the data from the pedometer 2 then it is significantly tedious and time consuming for the user to connect the "USB" cable to "USB" terminals on the pedometer.

What is claimed is:

1. A health care system, comprising:
one or more living body data measurement units wherein at least one unit includes a pedometer;
a receiver unit including a permanent magnet, an infrared ray receiving section, and a wireless receiving section; and
a personal computer;
wherein said living body data measurement unit measures living body data,
wherein said receiver unit receives the living body data from the living body data measurement unit,
wherein said pedometer includes a reed switch which turns on, responsive to the permanent magnet, when said pedometer is placed on said receiver unit, and sends the living body data to said receiver unit by infrared ray responsive to the reed switch turning on,
wherein said personal computer is USB connected to the receiver unit, and wherein said wireless receiving section is normally in standby condition and, upon receiving the living body data from the living body data measurement unit, checks whether there is any problem in the data, and if not, acquires the living body data.

2. A health care system according to claim 1 in which said receiver unit receives the living body data from the living body data measurement unit via electromagnetic wave or infrared ray.

3. A health care system according to claim 1 in which said living body data measurement unit includes at least one of a body fat meter and a sphygmomanometer.

4. A health care system according to claim 1, wherein the living body data measurement unit comprises a body fat meter, and said living body data includes at least one of body weight, body fat rate, body fat mass, basal metabolism, total energy consumption and visceral fat level.

5. A health care system according to claim 1, wherein said living body data includes at least one of number of steps, distance, calorie consumption and amount of burned fat.

6. A health care system according to claim 1, wherein the living body data measurement unit comprises a sphygmomanometer, and said living body data includes at least one of highest blood pressure, lowest blood pressure and pulse rate.

7. A health care system according to claim 1, wherein the living body data measurement unit comprises a body fat meter or a sphygmomanometer, and it sends the living body data to the receiver unit in a frame synchronized manner upon depressing a data transmission button after measurement is done.

* * * * *